United States Patent
Ambati et al.

(10) Patent No.: US 11,809,826 B2
(45) Date of Patent: Nov. 7, 2023

(54) ASSERTION DETECTION IN MULTI-LABELLED CLINICAL TEXT USING SCOPE LOCALIZATION

(71) Applicant: Siemens Healthcare GmbH, Erlangen (DE)

(72) Inventors: Rajeev Bhatt Ambati, Plainsboro, NJ (US); Oladimeji Farri, Upper Saddle River, NJ (US); Ramya Vunikili, Secaucus, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 532 days.

(21) Appl. No.: 16/949,838

(22) Filed: Nov. 17, 2020

(65) Prior Publication Data

US 2021/0174027 A1  Jun. 10, 2021

Related U.S. Application Data

(60) Provisional application No. 62/946,187, filed on Dec. 10, 2019.

(51) Int. Cl.
*G06F 40/00* (2020.01)
*G06F 40/30* (2020.01)
(Continued)

(52) U.S. Cl.
CPC .............. *G06F 40/30* (2020.01); *G06F 40/279* (2020.01); *G06N 3/08* (2013.01); *G16H 30/20* (2018.01);
(Continued)

(58) Field of Classification Search
CPC ........ G06N 20/00; G06N 20/10; G06N 3/044; G06N 3/08; G06N 20/20; G06N 3/02; G06N 3/04; G06N 3/042; G06N 3/045; G06N 3/0455; G06N 3/0464; G06N 3/047; G06N 3/0475; G06N 3/048; G06N 3/0499; G06N 3/088; G06N 3/0895; G06N 3/09; G06N 3/091; G06N 3/092; G06N 3/094; G06N 3/096; G06N 3/10; G06N 5/04; G06F 40/30; G06F 40/20; G06F 40/268; G06F 40/279; G06F 40/205; G06F 40/00; G06F 40/253; G06F 40/289; G06F 40/35;
(Continued)

(56) References Cited

U.S. PATENT DOCUMENTS

| | | | |
|---|---|---|---|
| 11,170,892 B1 * | 11/2021 | McKinney, IV | G16H 15/00 |
| 2009/0058860 A1 * | 3/2009 | Fong | G06F 40/103 |
| | | | 704/9 |

(Continued)

OTHER PUBLICATIONS

Pons, Ewoud, et al. "Natural language processing in radiology: a systematic review." Radiology 279.2 (2016): 329-343. (Year: 2016).*

(Continued)

*Primary Examiner* — Edgar X Guerra-Erazo

(57) ABSTRACT

For assertion detection from clinical text in a medical system, a model, such as a neural network, is trained to operate on multi-labeled clinical text. Using multi-task learning, both the scope and the class losses are minimized. As a result, a machine learning model can predict both the scope and class of clinical text for a patient where the clinical text is not limited to one class or a particular length.

20 Claims, 6 Drawing Sheets

(51) Int. Cl.
  G16H 50/20  (2018.01)
  G16H 30/20  (2018.01)
  G16H 30/40  (2018.01)
  G06N 3/08  (2023.01)
  G06F 40/279  (2020.01)
  G16H 70/60  (2018.01)
  A61B 6/00  (2006.01)
  A61B 6/03  (2006.01)

(52) U.S. Cl.
  CPC ............. *G16H 30/40* (2018.01); *G16H 50/20* (2018.01); *G16H 70/60* (2018.01); *A61B 6/032* (2013.01); *A61B 6/503* (2013.01)

(58) Field of Classification Search
  CPC . G10L 15/1815; G10L 15/1822; G10L 15/18; G10L 15/16
  See application file for complete search history.

(56) References Cited

U.S. PATENT DOCUMENTS

| | | | | |
|---|---|---|---|---|
| 2012/0232923 | A1* | 9/2012 | Carus | G16H 10/60 705/2 |
| 2014/0288973 | A1* | 9/2014 | Carus | G16H 10/60 705/3 |
| 2018/0150459 | A1* | 5/2018 | Farid | G06F 16/93 |

OTHER PUBLICATIONS

Koleck, Theresa A., et al. "Natural language processing of symptoms documented in free-text narratives of electronic health records : a systematic review." Journal of the American Medical Informatics Association 26.4 (2019): 364-379. (Year: 2019).*

McBee, Morgan P., et al. "Deep learning in radiology." Academic radiology 25.11 (2018): 1472-1480. (Year: 2018).*

Shin, Bonggun, et al. "Classification of radiology reports using neural attention models." 2017 international joint conference on neural networks (IJCNN). IEEE, 2017. (Year: 2017).*

Liao, Minghui, Baoguang Shi, and Xiang Bai. "Textboxes++: A single-shot oriented scene text detector." IEEE transactions on image processing 27.8 (2018): 3676-3690. (Year: 2018).*

Afzal, Zubair, et al. "ContextD: an algorithm to identify contextual properties of medical terms in a Dutch clinical corpus." BMC bioinformatics 15.1 (2014): 373.

Bhatia, Parminder, E. Busra Celikkaya, and Mohammed Khalilia. "End-to-end joint entity extraction and negation detection for clinical text." International Workshop on Health Intelligence. Springer, Cham, 2019.

Chapman, Wendy W., et al. "A simple algorithm for identifying negated findings and diseases in discharge summaries." Journal of biomedical informatics 34.5 (2001): 301-310.

Chen, Long. "Attention-based deep learning system for negation and assertion detection in clinical notes." International Journal of Artificial Intelligence and Applications (IJAIA) 10.1 (2019).

Cheng, Katherine, Timothy Baldwin, and Karin Verspoor. "Automatic negation and speculation detection in veterinary clinical text." In Proceedings of the Australasian Language Technology Association Workshop 2017, pp. 70-78. 2017.

Cotik, Viviana, et al. "Syntactic methods for negation detection in radiology reports in Spanish." Proceedings of the 15th Workshop on Biomedical Natural Language Processing, BioNLP 2016: Berlin, Germany, Aug. 12, 2016. Association for Computational Linguistics, 2016.

De Bruijn, Berry, et al. "Machine-learned solutions for three stages of clinical information extraction: the state of the art at i2b2 2010." Journal of the American Medical Informatics Association 18.5 (2011): 557-562.

Fancellu, Federico, Adam Lopez, and Bonnie Webber. "Neural networks for negation scope detection." Proceedings of the 54th annual meeting of the Association for Computational Linguistics (vol. 1: long papers). 2016.

Gkotsis, George, et al. "Don't let notes be misunderstood: A negation detection method for assessing risk of suicide in mental health records." Proceedings of the Third Workshop on Computational Linguistics and Clinical Psychology. 2016.

Konstantinos Sechidis, Grigorios Tsoumakas, and Ioan-nis Vlahavas. 2011. On the stratification of multi-label data. In Proceedings of the 2011 European Conference on Machine Learning and Knowledge Discovery in Databases—vol. Part III,ECML PKDD'11, pp. 145-158, Berlin, Heidelberg. Springer-Verlag.

MacKinlay, Andrew, David Martinez, and Timothy Baldwin. "Detecting modification of biomedical events using a deep parsing approach." BMC medical informatics and decision making. vol. 12. No. S1. BioMed Central, 2012.

Mehrabi, Saeed, et al. "DEEPEN: A negation detection system for clinical text incorporating dependency relation into NegEx." Journal of biomedical informatics 54 (2015): 213-219.

Peng, Yifan, et al. "Negbio: a high-performance tool for negation and uncertainty detection in radiology reports." AMIA Summits on Translational Science Proceedings 2018 (2018): 188.

Redmon, Joseph, et al. "You only look once: Unified, real-time object detection." Proceedings of the IEEE conference on computer vision and pattern recognition. 2016.

Rumeng Li, N. Jagannatha Abhyuday, and Yu Hong. "A hybrid neural network model for joint prediction of presence and period assertions of medical events in clinical notes." AMIA Annual Symposium Proceedings. vol. 2017. American Medical Informatics Association, 2017.

Shivade, Chaitanya, et al. "Extending NegEx with kernel methods for negation detection in clinical text." Proceedings of the Second Workshop on Extra-Propositional Aspects of Meaning in Computational Semantics (ExProM 2015). 2015.

Sohn, Sunghwan, Stephen Wu, and Christopher G. Chute. "Dependency parser-based negation detection in clinical narratives." AMIA Summits on Translational Science Proceedings 2012 (2012): 1.

Stenetorp, Pontus, et al. "BRAT: a web-based tool for NLP-assisted text annotation." Proceedings of the Demonstrations at the 13th Conference of the European Chapter of the Association for Computational Linguistics. 2012.

Sutskever, Ilya, Oriol Vinyals, and Quoc V. Le. "Sequence to sequence learning with neural networks." Advances in neural information processing systems. 2014.

Szymański, Piotr, and Tomasz Kajdanowicz. "A scikit-based Python environment for performing multi-label classification." arXiv preprint arXiv: 1702.01460 (2017).

Uzuner, Özlem, et al. "2010 i2b2/VA challenge on concepts, assertions, and relations in clinical text." Journal of the American Medical Informatics Association 18.5 (2011): 552-556.

Zhang, Yijia, et al. "BioWordVec, improving biomedical word embeddings with subword information and MeSH." Scientific data 6.1 (2019): 1-9.

* cited by examiner

FIG 7 imaging study unk cta coronary arteries w unk calcium scoring clinical statement
*present*     *present*                         *present*    *present*
unk diabetes unk hypertension unk impression unk 1 unk calcium score unk 3451
0.93                            0.97   0.73
unk see comments unk 2 unk injection portion of the examination was not performed
*present*                  *absent*
due to the amount of coronary artery calcification present unk technique unk due to
            0.75    0.58
the history af asthma and the patient having used his inhaler over the past week every
                                   *present*    *present*
day unk the patient was premedicated with medrol for this exam unk metoprolol 100
                         *conditional*                   0.89
mg po was administered prior to the scan to decrease heart rate unk despite this heart
0.78                                     0.76
rate was approximately 84 prior to the calcium score portion of the study unk there
*present*                 *present*    *present*                 *present*
is cardiac motion artifact present unk coronary artery calcium was quantified by
       0.72    0.92                   0.74    0.72
obtaining an agatston score from precontrast data unk because the coronary artery calcium score was exceedingly high unk the contrast injection portion of the study
                     *present*                      *present*
was not performed unk extracardiac soft tissues unk lungs unk no significant
                           0.81               0.86
abnormality unk calcium score unk 3451 unk there is some probable false evalution
                 *present*               *present*
of this number due to cardiac motion artifact unk as this patient unk s heart rate was
                                   0.96    0.71
high for this study however likely the true number lies between unk date this number

ASSERTION DETECTION IN MULTI-LABELLED CLINICAL TEXT USING SCOPE LOCALIZATION

RELATED APPLICATION

The present patent document claims the benefit of the filing date under 35 U.S.C. § 119(e) of Provisional U.S. Patent Application Ser. No. 62/946,187, filed Dec. 10, 2019, which is hereby incorporated by reference.

BACKGROUND

The present embodiments relate to natural language processing (NLP) of clinical text of medical data to detect an assertion. Assertion detection involves classifying clinical text obtained from the electronic health record (EHR) of a patient and/or other hospital information systems (e.g. Radiology Information System/RIS) to determine if a medical concept (entity) is of a particular class (e.g., present, absent, conditional, hypothetical, possibility or AWSE (associated with someone else)).

Advanced NLP techniques, including machine deep learning, have been applied to EHR documents to extract useful information to assist in diagnosis. Accessibility to large scale EHR data is crucial to using such deep learning methods, yet data scarcity persists for most tasks in the healthcare domain. As a result, the NLP of the clinical text is overly simplified. Past works mostly focused on the present and absent classes with comparatively less work on the more ambiguous classes. Either the given text only is classified, or the class is used to further to detect the scope in a two-stage process. These approaches may work well for datasets in which there exists only one label per example. However, single label per sentence is not a common phenomenon in clinical reports, especially when patients have frequent physician visits or long periods of hospitalization.

SUMMARY

Systems, methods, and instructions on computer readable media are provided for assertion detection from clinical text in a medical system. A model, such as a neural network, is machine trained to operate on multi-labeled clinical text. Using multi-task learning, both the scope and the class losses are minimized. As a result, a machine learning model can predict both the scope and class of clinical text for a patient where the clinical text is not limited to one class or a particular length.

In a first aspect, a method is provided for assertion detection from clinical text in a medical system. The clinical text is input to a machine learning model. Both a scope as a word group box and an assertion class for the word group box are identified from the clinical text. The machine learning model identifies both the word group box and the assertion class in response to the input. An image showing words of the word group box and the assertion class for the words is generated.

In one embodiment, the scope and assertion class are identified as a single stage, end-to-end operation of the machine learning model.

In one example, the input clinical text is a radiology report for a patient. The machine learning model may be of various types, such as a convolutional neural network.

To identify both scope and class, the machine learning model was trained as a multi-task model with a combination of an objective function for the scope and an objective function for the assertion class. The objective function for the scope may be a mean square error between predicted and ground-truth intersection over union. The objective function for the assertion class may be a cross entropy loss. The combination may be a sum or other function.

In one embodiment, the scope is identified by identifying a plurality of possible word groups by the machine learning model and identifying the scope with a non-max suppression of the possible word groups. In another embodiment, the scope is identified as a word group forming the word group box of a same class.

Various assertions may be classified. In one embodiment, the assertion classes are present, absent, conditional, hypothetical, possible, or associated with someone else. The assertion label for a given group of words may be identified as one of these assertion classes.

In a second aspect, a system is provided for assertion detection from clinical text. A memory is configured to store the clinical text for a patient. A processor is configured to separate the clinical text into multiple assertions. The clinical text is separated by a machine learning model being trained to localize a scope in the clinical text and assign a label for each of the assertions. The machine learning model was trained with multi-labelled data as a multi-task model. A display is configured to indicate the scope and class for each assertion.

In one embodiment, the machine-learned model is a convolutional neural network. In other embodiments, the machine-learned model was trained as the multi-task model with an objective function for the scope and an objective function for the class. In yet another embodiment, the processor is configured to select a localization of the scope output by the machine-learned model using non-max suppression.

In a third aspect, a method is provided for training a machine learning model for assertion detection. A neural network is trained to both detect both class and scope for each instance in clinical text. The neural network is trained using multi-labelled text as ground truth where the labels include the class and scope. The trained neural network is then stored for later application.

In one embodiment, the machine training performs multi-task learning with a combination loss of a first objective function for the class and a second objective function for the scope being minimized.

In another embodiment, the neural network being trained is a convolutional neural network.

The neural network may output various possible word groupings for the scope, so one of the possible word groupings is selected as the scope using non-max suppression.

In yet another embodiment, the neural network is a single stage, end-to-end solution for both the scope and the class.

Any one or more of the aspects described above may be used alone or in combination. Any aspects of one of method, system, or computer readable media may be used in the others of method, system, or computer readable media. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

FIG. 7 shows example results of predicted class and scope for a portion of clinical text.

DETAILED DESCRIPTION OF EMBODIMENTS

In clinical text, such as a radiology report or physician notes, single label per sentence is not a common phenomenon. For example, when patients have frequent physician visits or long periods of hospitalization, the resulting clinical text may have many different occurrences of entities of different classes, even in the same sentence. In one example, the clinical text is: "clinical statement: abnormal stress test, coronary artery calcium score 15 which places the patient at the $60^{th}$ percentile, no evidence of soft plaque or stenosis, 2 mm right upper lobe lung" This text may include four entities, such as "abnormal stress test," coronary artery calcium score," "soft plaque or stenosis," and "right upper lobe lung" of the classes present, present, absence, and present. Multiple labels extending over different scopes (e.g., numbers of words) are provided.

To address the multi-labelled clinical text, the assertion detection is cast as a scope localization problem thereby solving classification and scope detection in a single stage, end-to-end fashion. A machine learning model, such as a convolutional neural network, detects bounding boxes around class scopes as well as the label for each entity.

In one example, multi-labelled sentences (text) in the clinical domain, such as radiology reports based on cardiac computed tomography (CT) imaging, result from the rich description of scenarios during patient care. Rather than addressing the clinical text as single assertion label per sentence (text) and without negation or assertion scope detection, a machine learning model (e.g., a convolutional neural network) is trained to localize multiple labels and their scopes in a single stage end-to-end fashion. The machine learning model may perform at least 12% better than the state-of-the-art NLP on multi-labelled clinical text.

Figure 1:
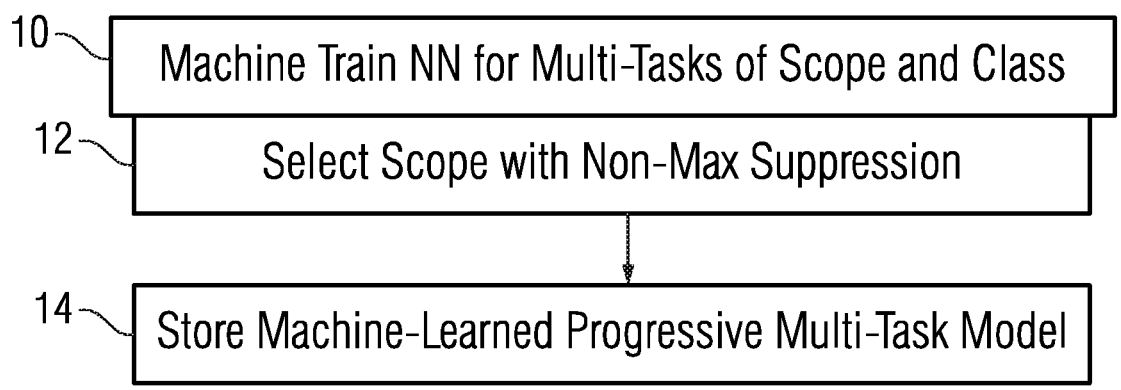
FIG. 1 is a flow chart diagram of one embodiment of a method for machine training with multi-labelled clinical text.

FIG. 1 is a flow chart diagram of one embodiment of a method for training a machine learning model for assertion detection. A machine learning model is trained to predict both scope and class at the same time. The model is trained to predict both given input clinical text, including text with multiple instances of entities to be classified.

The training is performed by a processor using training data (e.g., many examples of clinical text and corresponding ground truth classifications and scopes) stored in a database or another memory. Other devices may be used.

The acts are performed in the order shown or other orders. Additional, different, or fewer acts may be provided. For example, act 12 is not performed where the model is trained to select or output the scope with maximum probability. Acts for selecting training data and/or application of the trained model may be provided.

In act 10, the processor machine trains a model. The model, with learnable parameters, is defined. The training learns values for weights, connections, and/or other learnable parameters of the defined architecture. Various values for filter kernels may be learned. Different size kernels may be used. The weights, connections, filter kernels, and/or other parameters are the features being learned. Using the training data, the values of the parameters are adjusted and tested to determine the feature values leading to an optimum estimation of the output given an input sample. Adam or another optimization is used to train.

The model is trained to both detect class and detect scope for each instance in clinical text. The training data is multi-labelled text as the ground truth where the multi-labels include the class and the scope. The class is the assertion. Any number of classes may be distinguished, such as present and absent classes. For example, an entity of "aneurysm" is to be classified as being present or absent based on the clinical text. In one embodiment, the classes are present, absent, conditional, hypothetical, possibility, and associated with someone else (AWSE). Table 1 below shows examples of these six classes.

| Class | Examples |
|---|---|
| Present | Metoprolol 50 mg po was administered prior to the scan to decrease heart rate |
| Absent | No Chest pain, No Coronary artery Aneurysm, No Aneurysm or wall thickening |
| Conditional | Myocardial perfusion imaging, if not already performed, might improve specificity in this regard if clinically warranted |
| Hypothetical | Coronary plaque burden and focal Lesion characterization (if present) were assessed by visual estimate. |
| Possibility | This was incompletely imaged but suggests a diaphragmatic arteriovenous malformation |
| AWSE | High risk is > or = 10 packs/year or positive family history of lung cancer in first degree relative |

Other groups of classes may be used, such as using five, four, or three of the above listed classes. Other types of assertions (classes) may be used.

The scope is the extent or grouping of words associated with a given instance of the entity. In the example of the "present" class in Table 1, the scope is three words of "Metoprolol 50 mg." In the example of the "absent" class in Table 1, the scopes for the three instances are two words ("chest pain"), three words ("coronary artery aneurysm"), and four words ("aneurysm or wall thickening"). The scope is a localization of the instance of the class and may vary in extent or size depending on the clinical text.

The training data used for machine training includes many (tens, hundreds, or thousands) samples of clinical text and the ground truth. The ground truth is given by the multiple labels and includes designation of the class and the scope.

In one embodiment, the assertion and negation problem is formulated as follows. Let $R=\{r_1, r_2, \ldots, r_T\}$ be a sentence in clinical report consisting of T words $r_i$. The L assertion classes (e.g., six classes of Table 1) and corresponding scope in the report are to be identified. The assertion classes and the corresponding scope are defined by the set $S=\{(c_1, x_1, y_1), (c_2, x_2, y_2), \ldots, (c_L, x_L, y_L)\}$ where, class c, scopes between $x_i \in [1, T]$ and $y_i \in [1, T]$. x is the starting word and y is the finishing word of the scope or word group for an instance. The x and y values may define bounding boxes over the text that scope a particular class.

If A is the maximum scope of a class present in the input, prior boxes of lengths $\{1, 2, \ldots, A\}$ are placed at each word or token $r_i$. The prior boxes represent possible scope up to length A. The probability of a particular box containing a class is to be predicted. In one example, the text is "clinical statement: abnormal stress test." One box is from words 2-5 (i.e. "statement: abnormal stress test") and another box is from words 3-5 (i.e., "abnormal stress test").

An intersection over union (IoU) may be used in training the model to learn to predict scope. The union is the collection of all possible words in a set of bounding boxes for a given work. In the example in the paragraph above, the union is five words long. The intersection is the words in common. In the example in the paragraph above, the intersection is three words long. Let $B_1$, $B_2$ be two bounding boxes over text scopes $T_1$, $T_2$ where, $T_i$ is a set of words. The IoU of these two bounding boxes is as follows:

$$IoU(B_1 B_2) = \frac{|T_1 \cap T_2|}{|T_1 \cup T_2|} \quad (1)$$

where |S| is the cardinal of a set S.

For training the model, the model for machine learning is defined. The definition is by configuration or programming of the learning. The number of layers and/or units, type of learning, and other characteristics of the model are controlled by the programmer or user. In other embodiments, one or more aspects (e.g., number of nodes, number of layers or units, or type of learning) are defined and selected by the machine during the learning. In one embodiment, the model is defined as a neural network. Any neural network architecture may be used, such as a fully connected neural network or a convolutional neural network (CNN).

In one embodiment, a CNN is defined. The input sequence is embedded or defined in a distributional word vector space as $W=\{e_1, e_2, \ldots, e_T\}$ where, $e_i \in R^D$ is a column vector in an embedding matrix $E \in R^{T \times D}$. The network (e.g., CNN) is defined to operate on this input of the clinical data. Each layer in the CNN is a 1D-convolutional layer followed by a non-linearity. Stacking many layers on top of the other increases the receptive field of the network. To cover the largest prior box of length A, the receptive field of the last layer is at least A.

Figure 2:
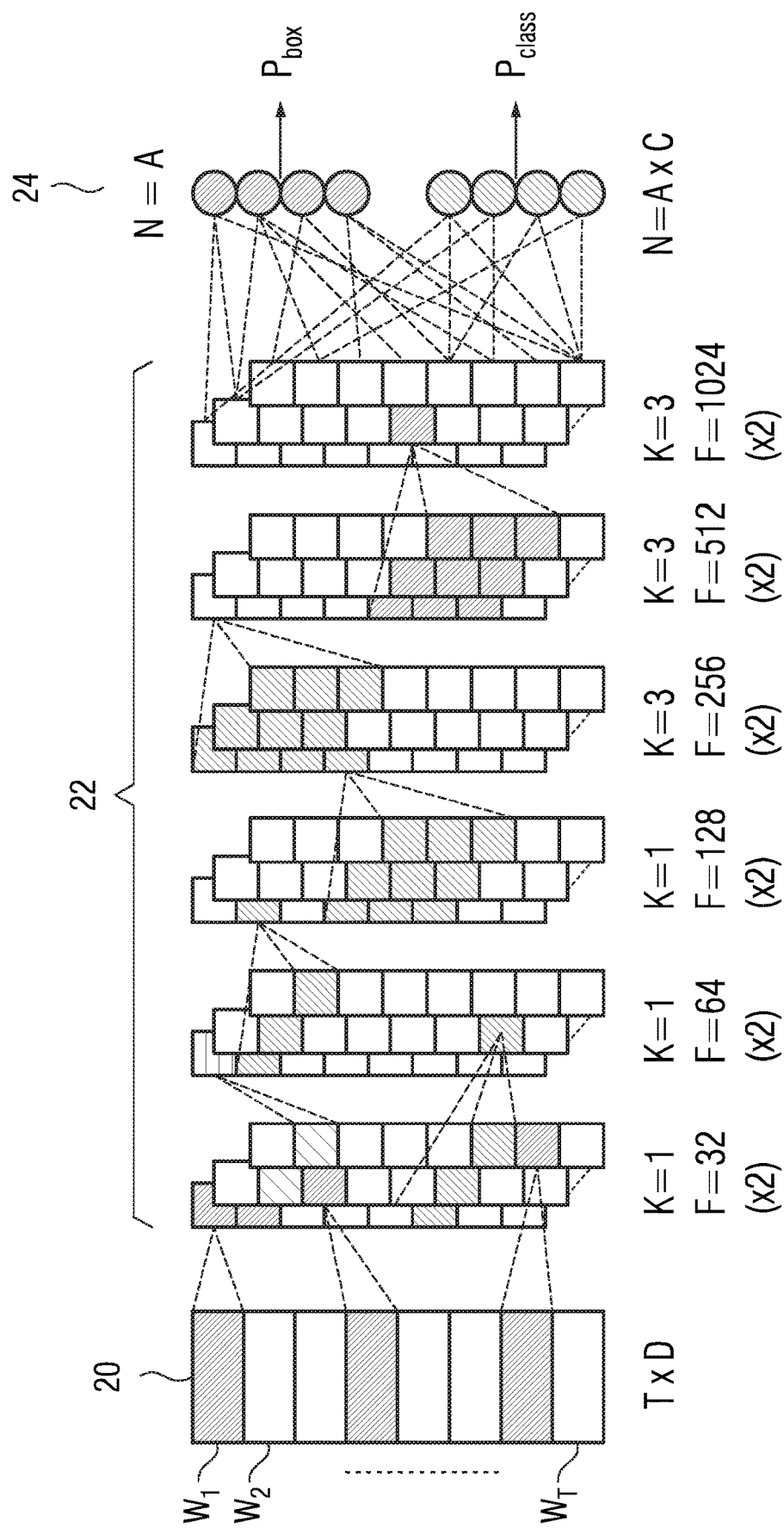
FIG. 2 is an example neural network for multi-task prediction.

Any arrangement of layers may be used. FIG. 2 shows an example. An embedding layer 20 receives the input sequence of the word vector. The embedding layer is pre-trained. The convolutional layers include 6 layers of 1×1 convolutions followed by 6 layers of 3×1 convolutions. The number of filters doubles every two layers. K, F, and N are kernel size, filter size, and the number of units, respectively.

A stride of 1 is used in training, but other stride values may be used. The feature maps are padded to maintain constant feature map size of T throughout the network. ReLU non-linearity is used after each convolutional layer. The output of the last convolutional layer is then passed through two branches of fully-connected layers to produce box confidence scores $p_{box} \in R^{T \times A}$ and class confidence probabilities $p_{class} \in R^{T \times A \times C}$ respectively. The feature map of the last convolutional layer is projected using two fully-connected layers of units A and A×C, respectively, where, A is the number of prior boxes and C is the number of classes. The receptive field of the last layer is 24 but may be another value of A or greater. In one example, the largest prior box in any of the classes is 20. Other networks may be defined, such as with additional, different, or fewer layers, with different kernel sizes, filter sizes, numbers of units, activation functions, input arrangements, and/or output arrangements.

The model is trained for multiple tasks. Multi-task machine learning is performed. The training optimizes the model for both tasks, such as estimation of scope and class. Multi-task learning is performed with a combination loss of a class objective function for the class and a scope objective function for the scope being minimized. In multi-task learning, a single network is defined that includes multiple outputs, such as the probability of class and box. Objective functions provide feedback in the machine learning. The objective functions represent or quantify the difference between the prediction and the ground truth. An aggregated objective is used for the multiple outputs in the training, so that the error in each task influences all the tasks. The training tries to perform each task at the same time, optimizing for the joint objective.

Any objective or loss function may be used for the scope. In one embodiment, the objective function for scope is given by a box confidence loss. The box confidence branch predicts the IoU of each prior box with the nearest ground truth box. The box confidence loss is a mean square error (MSE), but other loss may be measured. The Mean Square Error (MSE) between predicted and ground-truth IoU is minimized in training. An example MSE function may be represented as:

$$L_{box} = \frac{1}{TxA} \sum_{t=1}^{T} \sum_{a=1}^{A} \|p_{box}(t, a) - iou\|_2^2$$

Any objective or loss function may be used for the class. In one embodiment, the objective function for class is given by a class confidence loss. The class confidence branch is expected to predict P(class|box), the probability of a class given that a prior box has an assertion scope (i.e., probability of class for a given scope or box of words). Softmax is applied on the class confidence score, and cross-entropy loss is used to maximize the probability of the ground-truth class.

Where the training data has unequal instances of different classes, a weighted loss may be used. The weighted cross-entropy loss function may be represented as:

$$L_{class} = \frac{1}{TxA} \sum_{t=1}^{T} \sum_{a=1}^{A} \mathbb{1}_{box}^{a} \sum_{c=1}^{C} -\omega_c \mathbb{1}_c \log(p_{class}(c)) \quad (3)$$

where $\mathbb{1}$ is an indicator variable denoting the presence of a class in prior box-a and $\omega_c$ is the weight of class-c, which is equal to the fraction of examples in a batch that belong to class-c. Other weighting may be used.

For multi-task learning, a combination of the two or more losses is used in optimization. A cumulative loss L is a combination of the box loss ($L_{box}$) and class loss ($L_{class}$). Any combination may be used, such as a sum represented as $L=L_{box}+L_{class}$. Any optimization to minimize the combined loss may be used, such as an Adam optimizer. In alternative embodiments, progressive multi-task learning is used where one loss is first optimized and then the other loss is optimized.

Since there are multiple different prior boxes possible for a given instance of an entity, a box with a greatest confidence may be selected and used for the optimization. In another embodiment, the box (word group or scope) to be used for an instance is selected from the possible boxes (word groupings) for the given instance with non-max suppression as represented in act 12. Once the box confidence scores of T*A prior boxes are provided by the model for a given entity, the boxes are sorted in the decreasing order of their confidence scores. The boxes with confidence lower than a confidence threshold are discarded. In the remaining overlapping boxes, the prior box with the highest confidence score is selected and used. An example algorithm is provided by:

---

Algorithm 1: NonMaxSup(scores, priors)

---

Result: Final non-overlapping boxes
indices = ArgSort(scores);
boxes=[ ];
i = 0;
while i ≤ T * A do
  if scores(i) ≤ γ then
    break;
  else
    maxIoU
      ← max(IoU (prior s[i], boxes))
    if maxIoU = = 0 then
      boxes ← [boxes, prior s[i]] end
  end
  i ← i + 1
end

--- where γ is the threshold.

Since multi-task learning is used, the model is trained as a single stage, end-to-end solution for both the scope and the class.

One embodiment of the architecture defined as shown in FIG. 2 is trained for testing. To train with datasets having unbalanced classes, the sampling is stratified to represent the classes in the same ratio in training, validation, and testing sets. To further mitigate the effect of unbalanced classes in each batch of training data, the cross-entropy loss is weighted with the inverse of the number of examples for each class. The pre-trained embedded layer is from BioWord2Vec where the weights of this layer are frozen. Other embedded layers with or without pre-training may be used. The Adam optimizer with the default learning rate of 0.001 for 400 epochs is used. Shuffling after each epoch results in different distribution of classes per batch of iteration. This leads to unstable training so takes more epochs for convergence. The number of prior boxes is set to 24, a few more than the maximum length of the class scopes in the training set.

Figure 3:
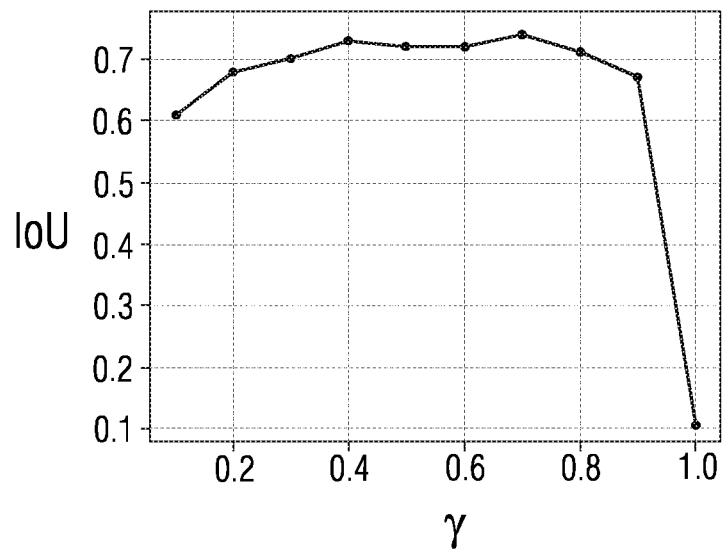
FIG. 3 shows an F1 score for performance of a machine learning model in scope prediction.

FIG. 3 shows the performance of the trained model on the validation set with different values of the IoU threshold (γ), the maximum being γ=0.7. The performance is measured as an F1 score of IoU. More layers and/or higher kernel sizes may or may not be used. Since the receptive field must be large enough (e.g., 24) to span the longest scope in the input, i.e., 20, increasing the number of layers and/or kernel sizes may not result in improved performance.

After training, the machine-learned model (e.g., CNN) is stored in act 14 (see FIG. 1). The weights, connections, kernels, and/or other features learned for the network are stored. The multi-task machine learning model is stored.

The stored model may be used or applied. Copies of the stored model may be used or applied by different servers, processors, computers, or workstations. In application, the clinical text for a given patient (e.g., patient's radiology report) is applied to the machine learning model, which outputs the scope and class of each instance in the clinical text. The output may assist in diagnosis and/or analysis for the patient or a medical institution or physician. The output may assist in automatically distilling information from large volumes of patient documents on the conditions that have been established as the patient's own diagnoses versus those that are being suspected or hypothesized, or those conditions that are related to family members. Such automation would improve the efficiency and accuracy of clinical decision-making for better patient management and outcomes, as well as support patient cohort selection for clinical trials and other forms of clinical research.

Figure 4:
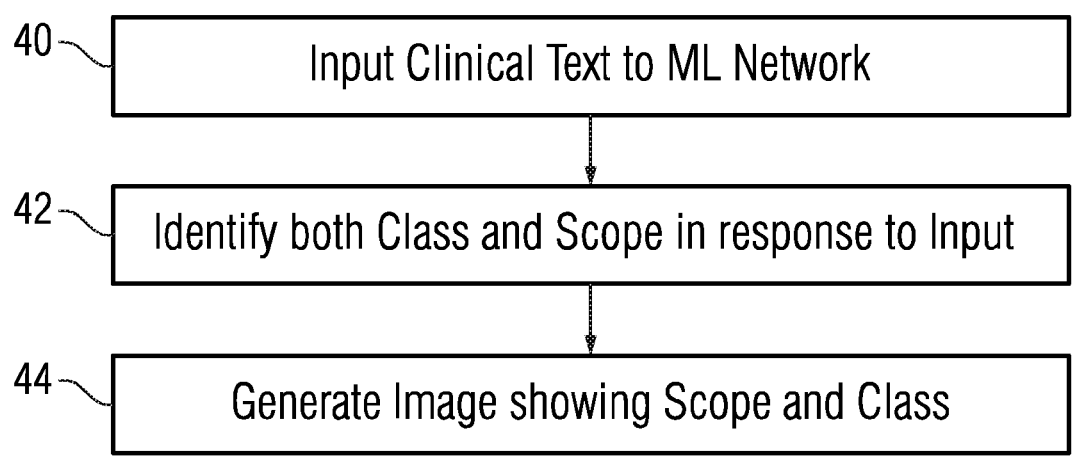
FIG. 4 is a flow chart diagram of one embodiment of a method for assertion detection from clinical text.

FIG. 4 is a flow chart diagram of one embodiment of a method for assertion detection from clinical text in a medical system. The medical system includes access to an electronic health record of a patient, such as through a database or local memory. The medical system also includes a processor, such as part of a computer, for application of a machine-learned model to predict both scope and class for any entities of the clinical text. The method of FIG. 4 is performed by the medical system of FIG. 8 or another system. Other devices may be used to perform any of the acts. In other embodiments, a server, workstation, or computer performs the method.

The method is performed in the order shown (e.g., top to bottom or numerical), but other orders may be used. Additional, different or fewer acts may be provided. For example, act 44 is not provided. As another example, acts for accessing an electronic health record are performed based on user input or other information. In yet another example, acts for using the scope and/or class to generate a report and/or provide a diagnosis, such as with another machine learning model, are included.

In act 40, a processor inputs clinical text to a machine learning model. The clinical text is an entire medical report, such as a radiology report. A portion of the report, such as just but all text, may be input. In other embodiments, a sentence or other sub-part of the available clinical text for a patient from one source is input. In another embodiment, clinical texts from multiple sources (e.g., a radiology report and physician notes) are input. Any source of clinical text may be used, such as a concatenation of fields from an electronic health records system, physician notes, radiology report, another report, or annotations.

The clinical text may be of any format, such as free text or structured text, as input. In other embodiments, the clinical text is reformatted into a word vector or another format. Punctuation may be removed or remain. Any filtering may be applied, such as to replace certain words.

The clinical text is input to the machine learning model. The clinical text is provided to the initial layer in the network, such as the pre-trained embedded layer 20 of FIG. 2.

The machine learning model is generic, such as a CNN trained as discussed for FIG. 1. For example, a neural network is used to regress the scope and class of any instances of entities in the input clinical text. A fully connected neural network, convolutional neural network, fully convolutional network, dense net, or another neural network may be used. In alternative embodiments, other machine learning models than a network may be used, such as a support vector machine, clustering based machine learning, Bayesian, or another machine-learned regressor.

The machine learning model receiving the input was previously trained as a multi-task network with a combination of an objective function for the scope and an objective function for the assertion class. Any objective functions may have been used, such as the objective function for the scope being a mean square error between predicted and ground-truth intersection over union and the objective function for the assertion class being a cross entropy loss. A combination, such as a sum, of these multiple objective functions was used to train the machine learning model with optimization and the training data. The input clinical text may be previously unseen (i.e., not in the training data) by the machine learning model.

In act 42, due to the training, the machine learning model outputs an identification of both the class and the scope in response to the input. The learned values of the trainable parameters of the model are applied to the input clinical text or features derived therefrom, resulting in output of the class and scope for each entity. Various features, such as filtered results from convolution operations or non-linear activations from outputs of convolution, are determined through a sequence of layers of the machine learning model, culminating in output of the probabilities of membership by class and of scope.

Different training settings, network architectures, training data, and/or type of training may result in a different machine learning model. The different machine learning models may output the same or different results.

The scope is identified as a word group box (i.e., group of words) of a same class. In one embodiment, one scope per entity is identified, so one scope per entity of one class is identified. In another embodiment, a plurality (e.g., up to A) of possible word groups is identified by the machine learning model for each entity. The probabilities output by the machine learning model for each prior box or possible word group are used to select one of the word groups as the scope. The maximum probability may be selected. Alternatively, a non-max suppression of the possible word groups is performed.

The class is identified as an assertion. The assertion for a given word group box or scope is identified from the clinical text by the machine learning model. Any group of assertion classes may be used, such as identifying a given instance of an entity as one of present, absent, conditional, hypothetical, possible, or associated with someone else. Every entity in the clinical text is identified as being of one of these types of assertions.

The class and scope are identified together in response to the input of the clinical text. The machine learning model identifies both the scope and the assertion class as a single stage, end-to-end operation of model.

In act 44, the processor generates an image showing the words of the word group box and the assertion class for the words for one or more entities. The output from the machine learning model is imaged. Alternatively, the output is further processed, such as rearranged or filtered, and the image is generated from the results of the further processing.

The image shows the scope, such as using highlighting, bold, font, italics, or the words of the scope alone. The image shows the class, such as annotation, color coding, labeling, or other designator of the class. For example, the clinical text is reproduced or loaded for viewing by a physician as part of the electronic health record. The different entities in the clinical text are indicated as scope (group of words) with an annotation of the class or type of assertion. This image may assist the physician in diagnosis, such as indicating the relevance through the assertion class and the locations of the relevant information in the text through the scope.

In alternative or additional embodiments, the output scopes and classes for the multiple entities of the clinical text are used to distinguish a patient's diagnoses from those that are related to other entities e.g. family members.

The machine learning model of FIG. 2 trained as discussed for FIG. 1 may perform better at multi-task identification of both class and scope in multi-labelled clinical text than the current state-of-the-art. The machine learning network (e.g., CNN for scope localization and class) is trained on clinical text from radiology reports for cardiac CT of two hospital sites (Dataset-I and Dataset-II). Both have radiology reports for cardiac CT with multi-labelled sentences. Datasets-I and II include 151 and 460 cardiac CT reports, respectively. The datasets are annotated by experts in labeling healthcare data. The annotations are done using the BRAT or another tool. Statistics of the data, such as the number of classes per report, number of tokens (substantive words) in a report, and length of class scopes, are shown in Tables 2-4, respectively.

TABLE 2

Distribution of Assertion classes in the data.

| Class | Dataset-I | | | Dataset-II | | |
| --- | --- | --- | --- | --- | --- | --- |
| | Train | Val | Test | Train | Val | Test |
| Present | 3711 | 511 | 524 | 17407 | 2215 | 2452 |
| Absent | 596 | 73 | 73 | 6136 | 708 | 805 |
| Conditional | 169 | 31 | 19 | 393 | 44 | 49 |
| Hypothetical | 147 | 22 | 18 | 69 | 10 | 5 |
| Possibility | 62 | 5 | 11 | 219 | 37 | 25 |
| AWSE | 15 | 3 | 2 | 21 | 4 | 2 |

TABLE 3

Number of tokens per report in the data.

| Split | Dataset-I | | | Dataset-II | | |
| --- | --- | --- | --- | --- | --- | --- |
| | Max | Min | Mean | Max | Min | Mean |
| train | 661 | 19 | 440 | 1028 | 82 | 610 |
| val | 642 | 289 | 452 | 911 | 82 | 630 |
| test | 560 | 228 | 432 | 968 | 336 | 642 |

TABLE 4

Scope lengths of each class per train, validation (val) and test splits.

| | Dataset-I | | | Dataset-II | | |
|---|---|---|---|---|---|---|
| Class | Train | Val | Test | Train | Val | Test |
| 1 | 3.36 ± 2.7 | 3.23 ± 2.50 | 3.39 ± 2.95 | 3.48 ± 2.15 | 3.38 ± 2.06 | 3.48 ± 2.16 |
| 2 | 2.79 ± 1.36 | 2.68 ± 1.25 | 2.68 ± 1.07 | 3.15 ± 2.26 | 3.10 ± 2.18 | 3.09 ± 2.13 |
| 3 | 2.85 ± 1.04 | 2.87 ± 0.87 | 2.68 ± 0.65 | 3.24 ± 2.95 | 3.20 ± 1.95 | 2.60 ± 1.74 |
| 4 | 5.05 ± 2.44 | 4.5 ± 2.44 | 5.0 ± 2.43 | 2.19 ± 1.21 | 2.60 ± 0.92 | 2.84 ± 2.47 |
| 5 | 3.14 ± 3.69 | 1.67 ± 0.47 | 3.27 ± 2.41 | 2.96 ± 2.83 | 2.40 ± 1.82 | 3.27 ± 2.41 |
| 6 | 2.47 ± 0.72 | 1.67 ± 0.47 | 5.5 ± 2.5 | 1.71 ± 1.35 | 2.00 ± 1.73 | 1.0 ± 0.0 |

Lengths are written in the format $\mu \pm \sigma$.

For comparison to the state-of-the-art, a baseline model is trained using the approaches of Bhatia et al., 2018 (Parminder Bhatia, Busra Celikkaya, and Mohammed Khalilia. 2018, "End-to-end joint entity extraction and negation detection for clinical text," *CoRR*, abs/1812.05270) and Chen, 2019 (Long Chen. 2019, "Attention-based deep learning system for negation and assertion detection in clinical notes"). Chen 2019 uses a bidirectional attentive encoder on the sentence input to obtain a context vector, which is subsequently passed to the softmax and output classification layers. Bhatia et al. 2018 extends this network by adding a shared decoder to predict both assertion class and named entity tag in a multi-task learning framework. However, the input to these seq2seq models is a sentence and the output prediction is a single class. Therefore, the models may not be easily extended to a multi-label dataset without compromising performance. To validate the assumption, the bidirectional encoder and attentive decoder model are extended based on long-short term memory (LSTM) to the multi-labelled data by changing the input format. In other words, instead of predicting one class for the entire input sequence, a class is predicted for each token so that the scope of a class can also be localized. Two sample sentences (with class labels) are shown in Table. 5. The two sample sentences have the label format for the baseline seq2seq model. P, C, H, N denote present, conditional, hypothetical and none classes, respectively.

TABLE 5

| Report-1 | Metoprolol$^P$ 50$^P$ mg$^P$ po$^N$ was$^N$ administered$^N$ prior$^N$ to$^N$ the$^N$ scan$^N$ to $^N$ decrease$^C$ heart$^C$ rate$^C$ |
|---|---|
| Report-2 | Myocardial$^H$ perfusion$^H$ imaging$^H$ ,$^N$ if$^N$ not$^N$ already$^N$ performed$^N$ ,$^N$ might$^H$ improve$^H$ specificity$^H$ in$^N$ this$^N$ regard$^N$ if$^N$ clinically$^N$ warranted$^N$ .$^N$ |

After training, the performance of the baseline model is compared to the performance of the model of FIG. 2. Table 6 shows the performance of the baseline and the CNN-based scope localization models on Datasets-I, II per class for the classes: Present, Absent, Conditional, Hypothetical, Possibility, and AWSE. Table 6 also shows a macro F1 score as the average over all classes.

TABLE 5

| | Model | | | |
|---|---|---|---|---|
| | Baseline | | Scope Localization model | |
| Class | Dataset-I | Dataset-II | Dataset-I | Dataset-II |
| Present | 0.97 | 0.92 | 0.90 | 0.84 |
| Absent | 0.27 | 0.34 | 0.84 | 0.93 |
| Conditional | 0.39 | 0.45 | 0.74 | 0.65 |
| Hypothetical | 0.76 | 0.69 | 0.87 | 0.75 |
| Possibility | 0.0 | 0.07 | 0.0 | 0.13 |
| AWSE | 0.42 | 0.39 | 0.60 | 0.0 |
| None | 0.81 | 0.89 | 0.96 | 0.95 |
| Macro | 0.52 | 0.53 | 0.70 | 0.61 |

The macro performance of the CNN model (scope localization model) is greater than the baseline model (e.g., 0.70 verses 0.52). This better performance may allow for more reliable assistance in diagnosis or analysis of clinical text through NLP.

Figure 5:
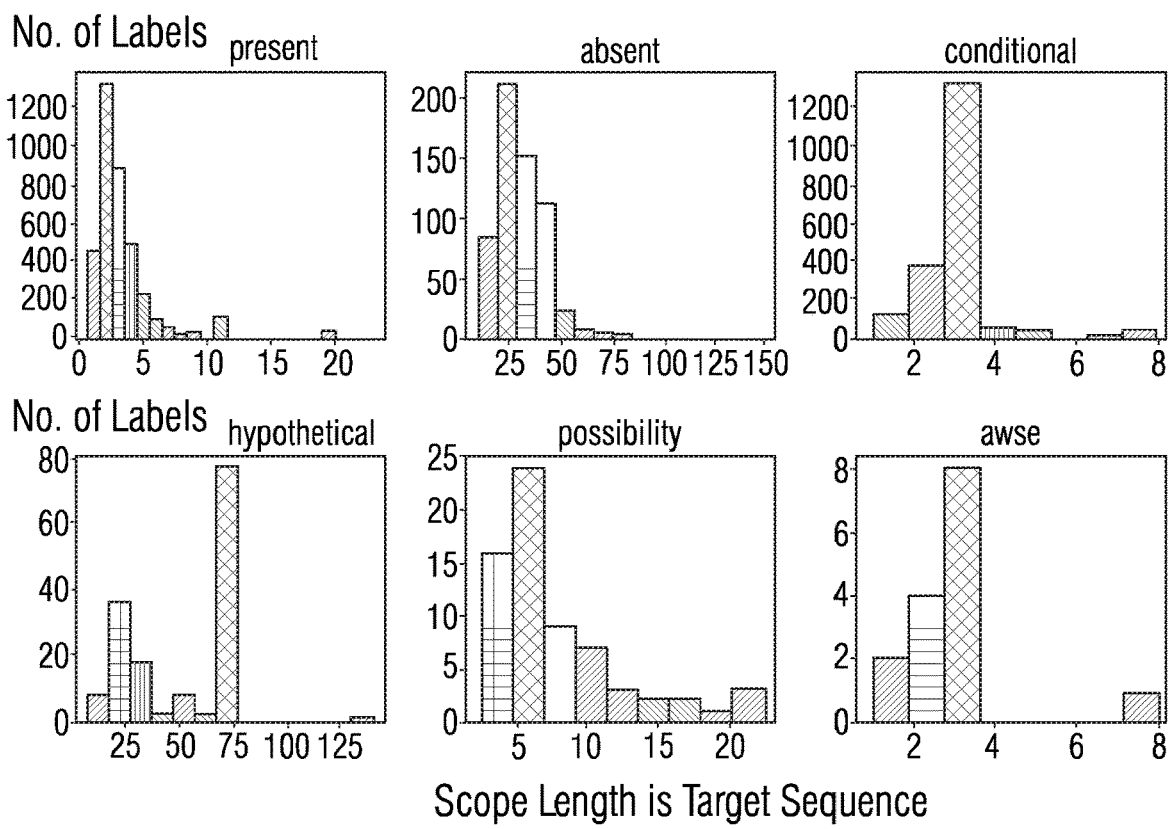
FIG. 5 shows example histograms of scope lengths per class.

For a fair comparison with the baseline, the box predictions from the CNN model are converted to a sequence of labels per token. The performance may be affected by the quantity of data available for training with the best performance on the "present" class and least performance on the "AWSE" class. The scope lengths found in the training set also contribute to performance. FIG. 5 shows a histogram of scope lengths available in the training set for each class.

Figure 6:
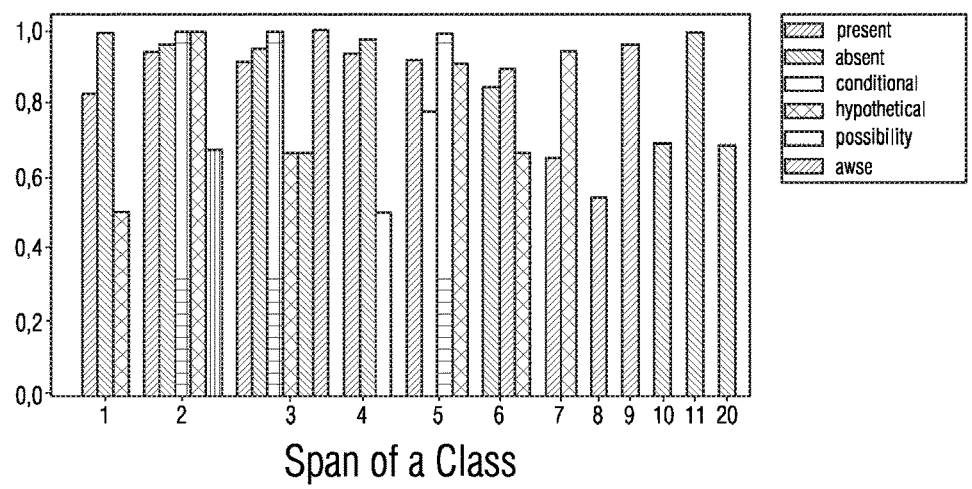
FIG. 6 illustrates the intersection over union between ground truth and predictions for different example classes.

The performance on the test set for different scope lengths is shown in FIG. 6. FIG. 6 shows the IoU (Intersection over Union) between the predictions and ground-truths on test set for different scope lengths. As shown, CNN model performance for the "present" class declines with scope lengths 7, 10, and 20, which reflect sparsity of this class for these scopes in the training set. In contrast, the CNN model performs well on the "hypothetical" class with scope length 7, reflective of the better distribution of this class for this scope relative to other scopes.

FIG. 7 shows a sample output of the CNN model on part of a radiology report from Dataset-I. The ground-truths are shown in solid boxes. The dashed boxes are prior boxes each having a box-confidence score as an annotation (e.g., "hypertension" having 0.93 confidence in a [0,1] scale). After non-max suppression of these prior boxes, the final predictions are shown in dotted line. Labels are italics with the underlined italics being the predicted label and the ground truth not being underlined. "unk" represents an unknown token (i.e., "unk" is used to represent the words that are not found in the vocabulary).

The scope localization model formed by the CNN allows operation on multi-label text. Since clinical data in the medical environment often includes multi-label text, the scope localization model allows NLP of clinical text with sufficient performance to realize useful assistance. Different inception layers (e.g., numbers of outputs) and/or different sets of kernel sizes in each layer may increase performance. The output layer would then have varying receptive fields (i.e., scope lengths), increasing the generalization of the model to scope lengths that are unseen in the training data.

Figure 8:
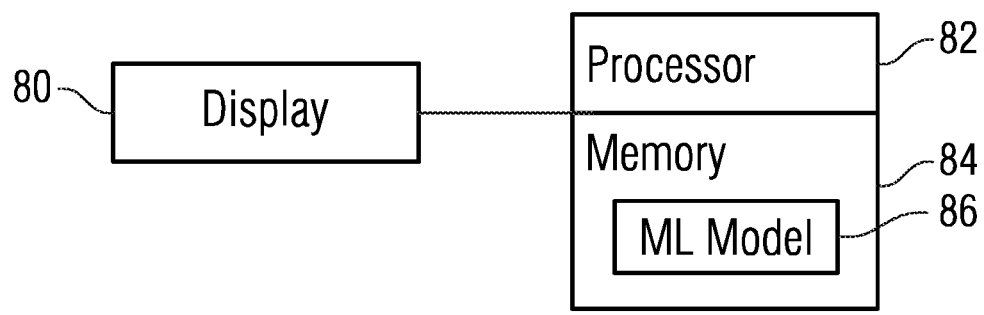
FIG. 8 is a block diagram of one embodiment of a medical system for assertion detection from clinical text.

FIG. 8 is a block diagram of one embodiment of a system for assertion detection from clinical text. The medical system includes the display 80, memory 84, and processor 82. The display 80, processor 82, and memory 84 may be part of a medical scanner, computer, server, workstation, or another system for processing clinical text from examination of a patient.

Additional, different, or fewer components may be provided. For example, a computer network is included for communication between remote components. The machine-learned model 86 is applied as a standalone application on the processor 82 or as a service deployed on network (cloud) architecture. As another example, a user input device (e.g., keyboard, buttons, sliders, dials, trackball, mouse, or other device) is provided for user interaction. In another example, a medical scanner (e.g., CT scanner) may be included for generating the images used for a radiology report.

The machine learning model, feature values, clinical text for a patient, scope, class, and/or other information are stored in a non-transitory computer readable memory, such as the memory 84. The memory 84 is an external storage device, RAM, ROM, database, and/or a local memory (e.g., solid state drive or hard drive). The same or different non-transitory computer readable media may be used for the instructions and other data. The memory 84 may be implemented using a database management system (DBMS) and residing on a memory, such as a hard disk, RAM, or removable media. Alternatively, the memory 84 is internal to the processor 82 (e.g. cache).

The instructions for implementing the training or application processes, the methods, and/or the techniques discussed herein are provided on non-transitory computer-readable storage media or memories, such as a cache, buffer, RAM, removable media, hard drive or other computer readable storage media (e.g., the memory 84). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

The processor 82 is a controller, control processor, general processor, digital signal processor, graphics processing unit, application specific integrated circuit, field programmable gate array, artificial intelligence processor, digital circuit, analog circuit, combinations thereof, or other now known or later developed device for processing clinical text. The processor 82 is a single device, a plurality of devices, or a network of devices. For more than one device, parallel or sequential division of processing may be used. Different devices making up the processor 82 may perform different functions, such as a processor for application of the machine-learned model 86 and another processor for formatting the input and/or processing the output. The processor 82 operates pursuant to and is configured by stored instructions, hardware, and/or firmware to perform various acts described herein.

The processor 82 or other remote processor is configured to train a machine learning architecture. Based on a user provided or another source of the network architecture and training data, the processor 82 learns to relate one or more input variables (e.g., clinical text) to outputs (e.g., scope and class probabilities). The training is multi-task. The result of the training is a machine learning model 86 for identifying scope and class in clinical text with multiple entities.

Alternatively or additionally, the processor 82 is configured to apply the machine learning model 86. In response to input of clinical text for a particular patient, the machine learning model 86 outputs a value or values indicating scope and the class for each instance. The machine learning model 86 separates the clinical text into multiple assertions, each having scope and class. The scope in the clinical text is localized for each of the assertions, and the class for each of the assertions is provided. Since the machine learning model 86 was trained with multi-labelled data as a multi-task model, the scope and assertion for multiple entities is output.

The machine learning model 86 is a convolutional neural network, but other model architectures or types may be used. The machine learning model 86 was trained as a multi-task model with an objective function for the scope and an objective function for the class.

The processor 84 may be configured to format the clinical text and/or select output of the machine learning model 86. For example, the processor 84 is configured to select a localization of the scope output by the machine learning model 86 using non-max suppression. As another example, the processor 84 is configured to generate an image, such as a list or report, that includes the estimated scopes and assertions.

The display 80 is a CRT, LCD, projector, plasma, printer, tablet, smart phone, or another now known or later developed display device for displaying the output, such as an image showing the scope and the class for each assertion. The image may show the scope and class in the report or clinical text or may show the scope and class by extraction of particular instances (e.g., in a list or spreadsheet). The scope and class are provided for multiple, some, each, or all the instances of entities in the clinical text, such as providing scope and class for each of multiple assertions in one sentence.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for assertion detection from clinical text in a medical system, the method comprising:
    inputting the clinical text to a machine learning model;
    identifying both a scope as a word group box and an assertion class for the word group box from the clinical text, the machine learning model identifying both the word group box and the assertion class in response to the inputting; and
    generating an image showing words of the word group box and the assertion class for the words.

2. The method of claim 1 wherein inputting the clinical text comprises inputting a radiology report for a patient.

3. The method of claim 1 wherein inputting comprises inputting to the machine learning model, the model comprising a convolutional neural network.

4. The method of claim 1 wherein inputting comprises inputting to the machine learning model, the model having been trained as a multi-task model with a combination of an objective function for the scope and an objective function for the assertion class.

5. The method of claim 4 wherein the objective function for the scope comprised a mean square error between predicted and ground-truth intersection over union.

6. The method of claim 4 wherein the objective function for the assertion class comprised a cross entropy loss.

7. The method of claim 4 wherein the combination comprises a sum.

8. The method of claim 1 wherein identifying the scope comprises identifying a plurality of possible word groups by the machine learning model and identifying the scope with a non-max suppression of the possible word groups.

9. The method of claim 1 wherein identifying the scope comprises identifying the scope as a word group forming the word group box of a same class.

10. The method of claim 1 wherein identifying the assertion class comprises identifying the assertion class as one of present, absent, conditional, hypothetical, possible, or associated with someone else.

11. The method of claim 1 wherein identifying comprises identifying both the scope and the assertion class as a single stage, end-to-end operation of the machine learning model.

12. A system for assertion detection from clinical text, the system comprising:
    a memory configured to store the clinical text for a patient;
    a processor configured to separate the clinical text into multiple assertions, the clinical text separated by a machine learning model configured to localize a scope in the clinical text for each of the assertions and a class for each of the assertions, the machine learning model having been trained with multi-labelled data as a multiple-task model; and
    a display configured to indicate the scope and class for each assertion.

13. The system of claim 12 wherein the machine learning model comprises a convolutional neural network.

14. The system of claim 12 wherein the machine learning model was trained as the multi-task model with an objective function for the scope and an objective function for the class.

15. The system of claim 12 wherein the processor is configured to select a localization of the scope output by the machine learning model using non-max suppression.

16. A method for training a machine learning model for assertion detection, the method comprising:
    machine training a neural network to both detect assertion class and scope for each instance in clinical text, the machine-training using multi-label text as ground truth where the multi-labels include the assertion class and the scope;
    storing the trained neural network.

17. The method of claim 16 wherein machine training comprises performing multi-task learning with a combination loss of a first objective function for the assertion class and a second objective function for the scope being minimized.

18. The method of claim 16 wherein machine training the neural network comprises machine training a convolutional neural network.

19. The method of claim 16 further comprising selecting from possible word groupings as the scope with non-max suppression.

20. The method of claim 16 wherein machine training comprises machine training as a single stage, end-to-end solution for both the scope and the assertion class.

* * * * *